(12) United States Patent
Ziman

(10) Patent No.: US 8,721,628 B2
(45) Date of Patent: May 13, 2014

(54) MEDICAL COUPLING SYSTEM

(75) Inventor: Lynn A. Ziman, Swanzey, NH (US)

(73) Assignee: Smiths Medical ASD, Inc., Rockland, MA (US)

( * ) Notice: Subject to any disclaimer, the term of this patent is extended or adjusted under 35 U.S.C. 154(b) by 1295 days.

(21) Appl. No.: 12/289,264

(22) Filed: Oct. 23, 2008

(65) Prior Publication Data

US 2009/0102192 A1  Apr. 23, 2009

Related U.S. Application Data

(62) Division of application No. 10/915,574, filed on Aug. 11, 2004, now Pat. No. 7,497,484.

(51) Int. Cl.
*A61M 25/16* (2006.01)

(52) U.S. Cl.
USPC .......................................... 604/534; 604/538

(58) Field of Classification Search
USPC .................. 604/513, 533, 534, 535, 538, 539
See application file for complete search history.

(56) References Cited

U.S. PATENT DOCUMENTS

| | | | |
|---|---|---|---|
| 1,871,370 A | 8/1932 | Jacques | |
| 3,287,031 A | 11/1966 | Simmons | |
| 5,651,776 A * | 7/1997 | Appling et al. | ............... 604/534 |
| 5,741,084 A | 4/1998 | Del Rio et al. | |
| 6,402,207 B1 | 6/2002 | Segal et al. | |
| 6,612,624 B1 | 9/2003 | Segal et al. | |
| 6,786,131 B2 | 9/2004 | Tsai | |
| 7,240,927 B2 | 7/2007 | Chang | |
| 7,270,349 B2 | 9/2007 | Bamberger et al. | |

FOREIGN PATENT DOCUMENTS

JP    2001-187990    7/2001

OTHER PUBLICATIONS

Chinese Office Action issued Apr. 6, 2012 for CN Appln No. 2011101192607, including English translation.
Canadian Office Action issued Apr. 13, 2012 for CA Appln No. 2,575,136.

* cited by examiner

*Primary Examiner* — Bhisma Mehta
(74) *Attorney, Agent, or Firm* — Louis Woo

(57) ABSTRACT

An adapter that bridges the connecting ends of a medication providing device and a fluid connector includes a housing shroud that is fitted at one end with a core and at its other end with an inner shroud. Once fitted to the housing shroud, the core and the inner shroud each are not removable from the housing shroud. A catch hub is provided within the housing shroud for non-removably maintaining the core to the housing shroud. The core is rotatable relative to the housing shroud.

16 Claims, 5 Drawing Sheets

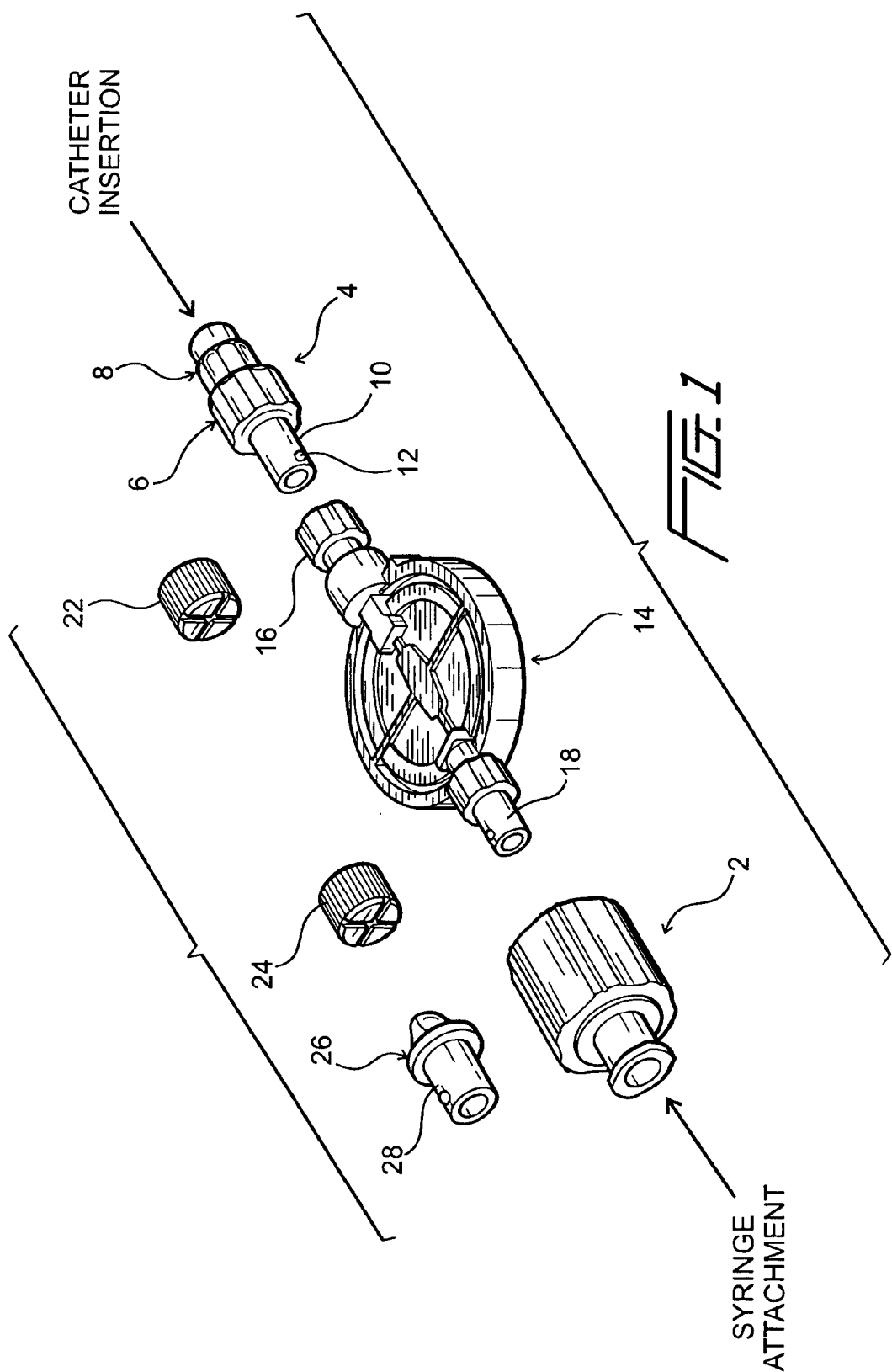

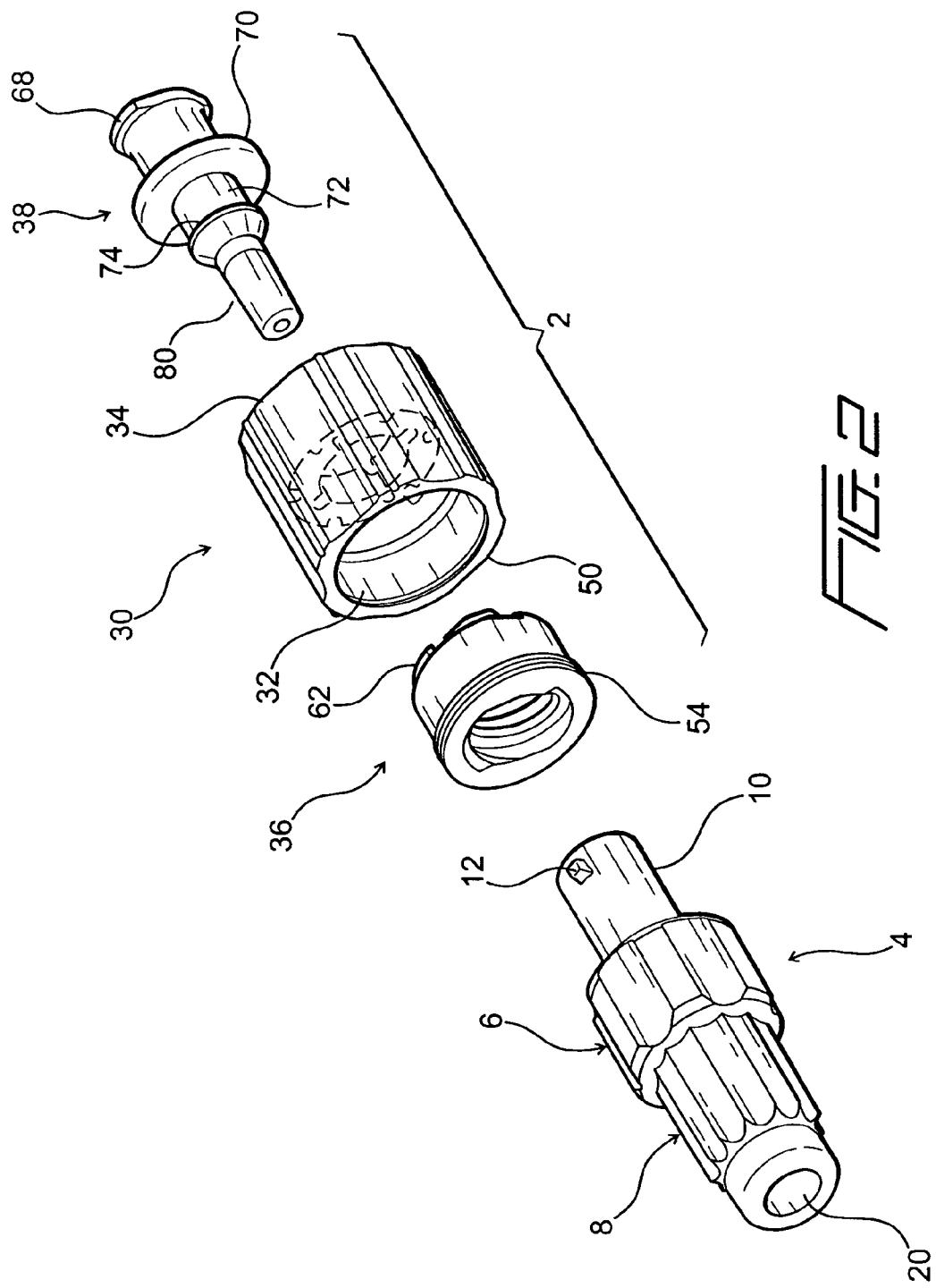

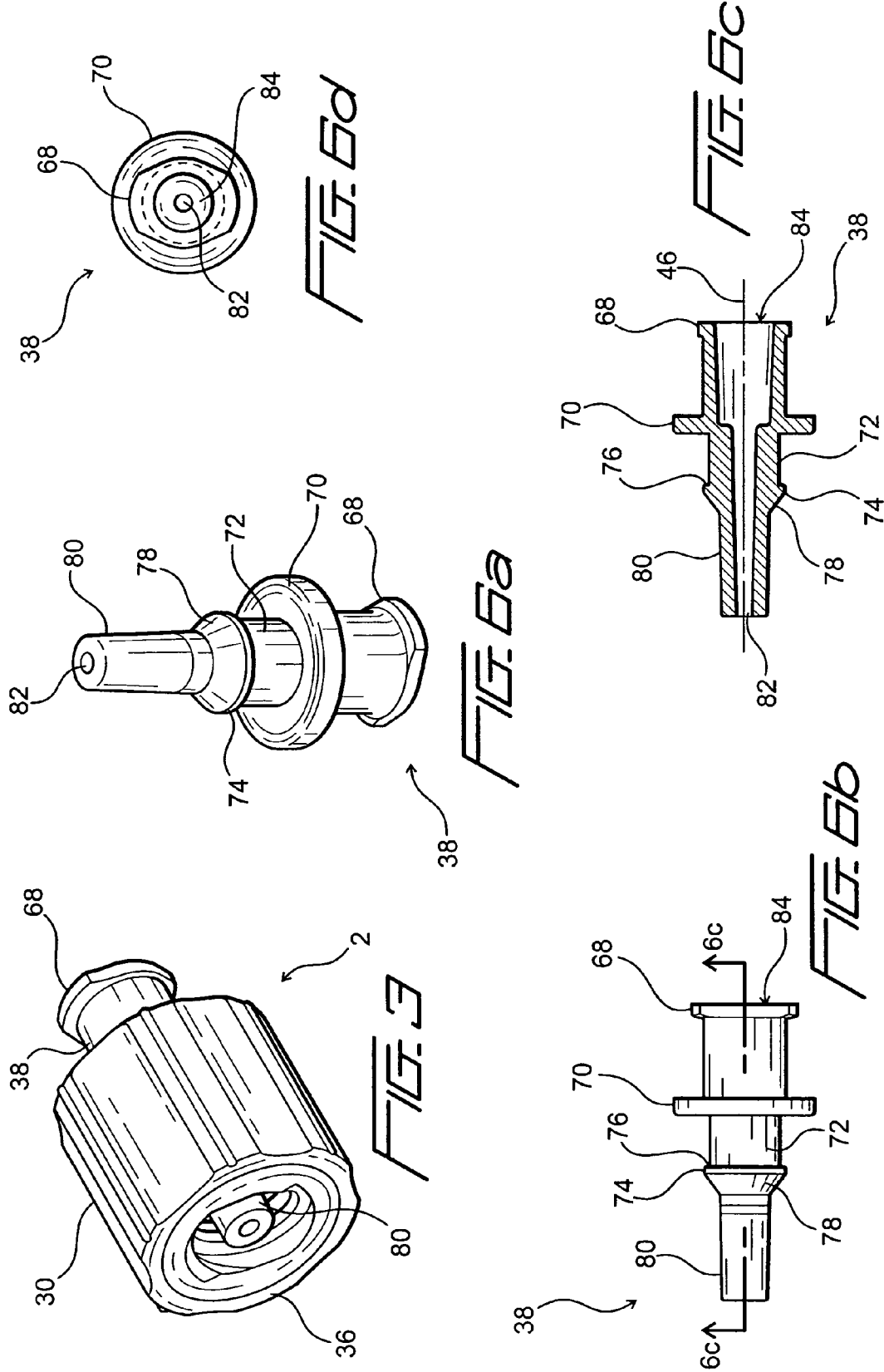

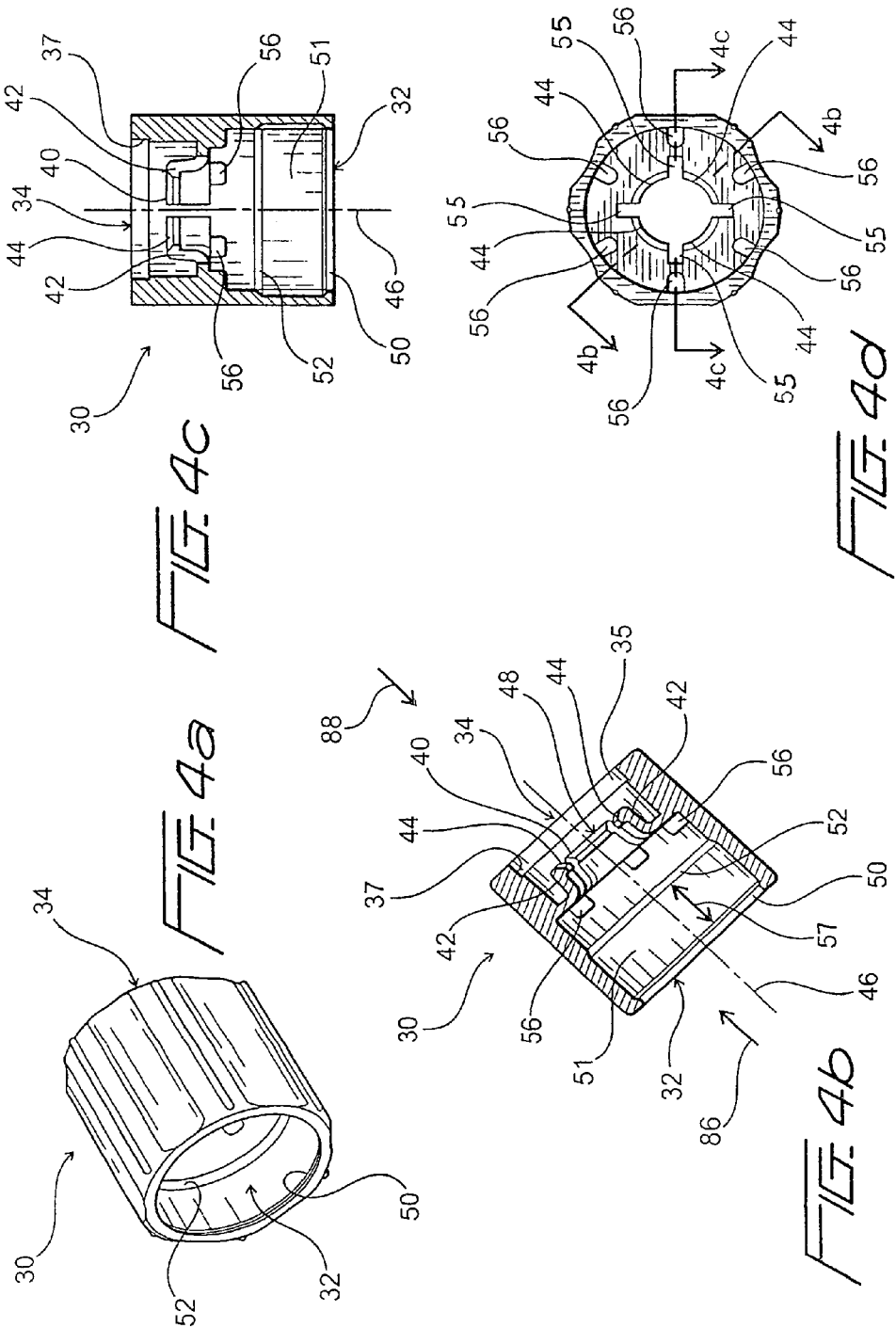

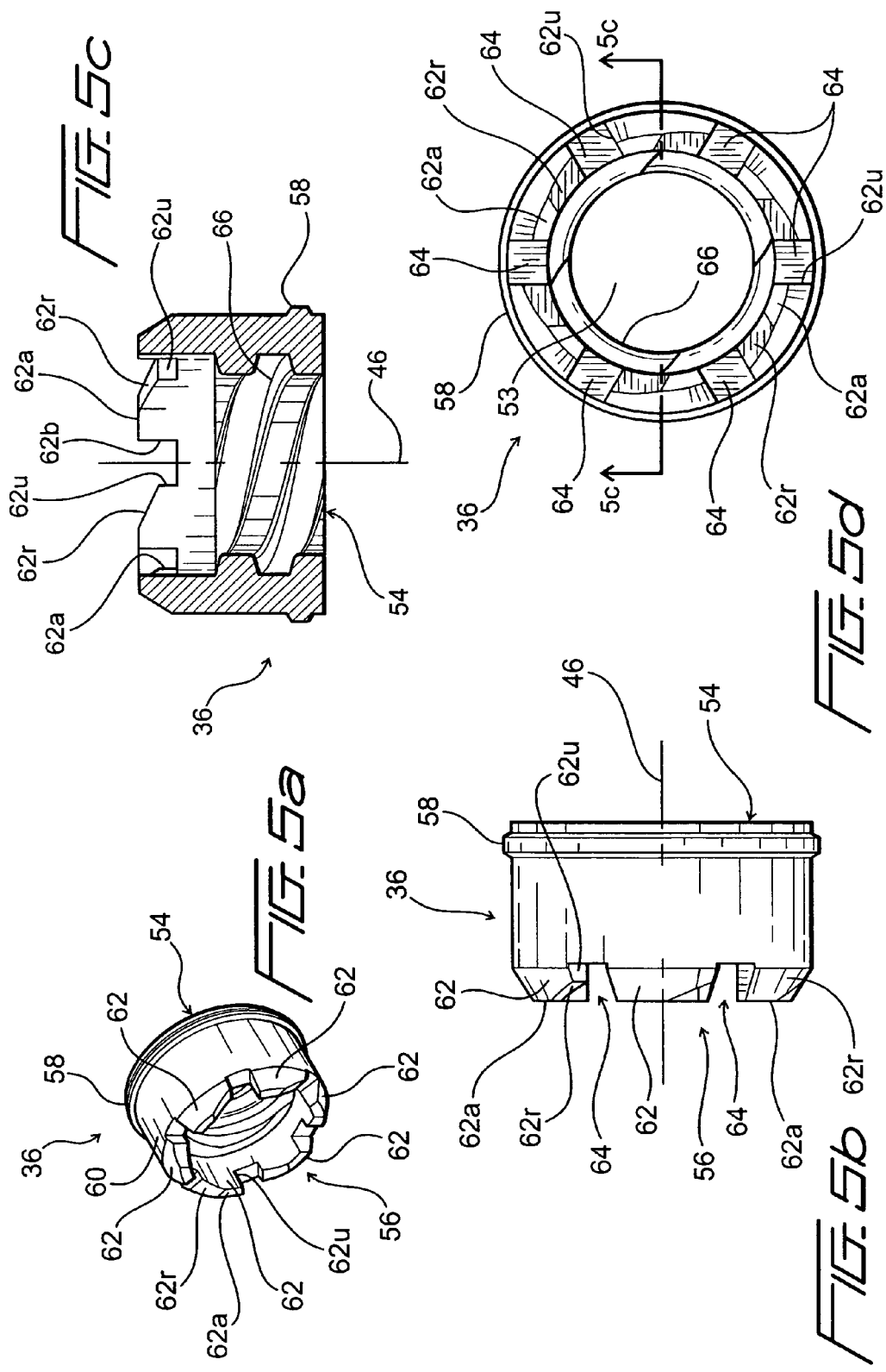

MEDICAL COUPLING SYSTEM

This is a divisional application of application Ser. No. 10/915,574 filed on Aug. 11, 2004, since issued as U.S. Pat. No. 7,497,484.

FIELD OF THE INVENTION

The present invention relates to connectors for a fluid path, and more particularly an adapter for coupling a medication providing device with a connector for providing medication to a patient.

BACKGROUND OF THE INVENTION

To prevent mis-connection of a fluid line to a device containing a particular medication, it has been shown in the prior art that a connector may be made up of two portions, with the portions being connected by complementary configured opposing surfaces. Such two portions connector ensures that the one line from one portion of the connector would not be wrongly connected to a different medication line. A fastening mechanism comprised of such complementary connecting portions is disclosed in U.S. Pat. No. 6,612,624 and its parent U.S. Pat. No. 6,402,207. The '624 patent discloses in particular a ratchet mechanism, as part of the connector, that prevents or impedes the uncoupling of one portion of the connector from a syringe to which the other portion may be connected. In practice, since the ratchet mechanism is dependent on the interaction of the teeth on the inner surface of an outer sleeve with a pawl of an inner body that fits into the outer sleeve, if the syringe were to be tightened too forcefully, the inner body would pop out of the outer sleeve. Moreover, as disclosed in the '624 patent, the ratchet mechanism is a portion of the connector that does not fully isolate the relative rotation of the outer sleeve and the inner body.

SUMMARY OF THE PRESENT INVENTION

The instant invention adapter is adapted to be interposed between a medication providing device and a connector. The adapter is designed to prevent the medication providing device from being removed therefrom, once the device is secured to one end of the adapter. The other end of the adapter is configured to accept a connector. The connector is rotatably connected to the adapter in one direction. Once fully connected, any further rotational movement along the same direction would simply cause the connector to rotate freely relative to the adapter. With a rotational motion in a counter direction, the connector can be removed from the adapter.

The adapter of the instant invention includes an outer cylindrical sleeve or a housing shroud that has an internal circumferential hub catch. In addition, a plurality of bumps extend from the inner wall of the housing shroud toward the central axis of the shroud. Fitted to this housing shroud is a cylindrical inner shroud that has a protrusion circumferentially formed proximate to its distal end that snap-mates to a circumferential groove formed at the distal end of the shroud. The inner shroud and the housing shroud are rotatable relative to each other.

A plurality of teeth extend from the proximal end of the inner shroud. When biased by a given force, these teeth of the inner shroud would act against the bumps extending from the inner wall of the housing shroud to prevent the inner shroud from rotating relative to the housing shroud. The extending teeth have inclining ramps that prevent the teeth from acting against the bumps, thereby allowing the two shrouds to rotate freely relative to each other when the biasing force is removed. The inner shroud may be internally threaded for accepting a specially designed connecting end of the connector.

A third component of the adapter of the instant invention is a core that fits to the housing shroud from the latter's other end. The core has a cylindrical central portion defined by a chamfered flange and a ring-shaped flange. This cylindrical central portion mates with the hub catch of the housing shroud that has a number of fingers configured to allow the chamfered flange to pass through but prevent the chamfered flange, the back of which is flat, from passing in the reverse direction. Thus, once the central portion of the core mates with the hub catch, the core is non-removably fitted to, but rotatable freely relative with, the housing shroud. The respective dimensions of the cylindrical central portion of the core and the opening formed by the hub catch fingers are configured to allow the core to rotate freely relative to the housing shroud. With the core fitted to the housing shroud, a medication providing device can be mated to the proximal end of the core.

The connector, for example a luer connector, of the medication providing device allows the medication providing device such as a syringe to be mated to the proximal connector of the core. Once the medication providing device is mated to the core, if a user were to try to remove the medication providing device from the core by applying a counter torque to the medication providing device, the core will rotate freely along the direction of the counter torque. The medication providing device is therefore prevented from being removed from the adapter. Additional torque in the direction that mates the medication providing device to the core does not cause any additional tightening, as the core will also rotate freely relative to the shroud. Thus, once the medication providing device is mated to the core, it could not be removed therefrom.

The instant invention therefore relates to an adapter for use with a medication providing device and a connector for providing medication to a patient. The adapter includes a housing shroud and an inner shroud fitted to the housing shroud. The inner shroud has an opening for accepting a connecting end of the connector such that the connector, once mated to the inner shroud, is freely rotatable in one direction and is removable from the inner shroud when rotated in a counter direction. The adapter further includes a core fitted in the housing shroud to allow the medication to be routed from the medication providing device to the connector. The core has a proximal end for enabling the medication providing device to be connected to the adapter. The medication providing device is not removable from the adapter once it is connected thereto.

The present invention also relates to a combination of a shroud having two open ends and an inner shroud non-removably fitted into one of the open ends of the shroud. The inner shroud has a connector end for enabling it to be mated to a given medication conveying connector. The inner shroud is rotatable freely in one direction once the given connector is mated thereto. The given connector is removable from the inner shroud when it is rotated in a counter direction. The combination further includes a core that is non-removably fitted to the other end of the shroud. The core has a through passage and a connector end for enabling the core to be mated to a luer connector of a medication providing device. The medication providing device, once mated to the connector end of the core, is not removable from the core.

The instant invention also relates to a method of routing a medication from a given medication providing device that includes the steps of providing a given medication conveying connector, providing an adapter having a shroud with one and other open ends, non-removably fitting an inner shroud into one end of the shroud and non-removably fitting a core into the other end of the shroud. The inner shroud has a connector end that enables the inner shroud to be mated to the given medical conveying connector, while the core has a through passage and a connector end for enabling it to be mated to the connector of the medication providing device that, once mated to the connector end of the core, is not removable from the core.

BRIEF DESCRIPTION OF THE FIGURES

The present invention will become apparent and the invention itself will be best understood with reference to the following description of the present invention taken in conjunction with the accompanying drawings, wherein:

FIG. 1 is an illustration of an exemplar overall path through which a medication is provided to a patient, with the various components being shown;

FIG. 2 is a perspective view of the adapter of the instant invention, with its components in alignment but not assembled, and a connector for conveying fluid to a patient;

FIG. 3 is a perspective view of the adapter of the instant invention in which the components have been assembled;

FIGS. 4A-4D are different views of the housing shroud of the adapter of the instant invention;

FIGS. 5A-5D are different views of the inner shroud of the adapter of the instant invention; and FIGS. 6A-6D are different views of the core of the adapter of the instant invention.

DETAILED DESCRIPTION OF THE INVENTION

As shown in FIG. 1, the adapter of the instant invention, designated 2, is connected to a connector 4, which is shown to include two portions 6 and 8. Portion 6 has a given connector end 10 that has a pair of projections 12 that enable connector end 10 to be mated to adapter 2. Connector end 10 may also be connected to a female end of a connector such as luer connector 16 of filter 14 shown in FIG. 1. Filter 14 is interposed between connector 4 and adapter 2 for filtering out contaminants that may be present in the medication or fluid that passes from a medication providing device, such as for example a syringe or a pump, to connector 4. Filter 14, in addition to luer connector 16, also has a second connector 18 that has a configuration similar to that of connector end 10 of connector 4, so as to enable filter 14 to be coupled to adapter 2.

In the embodiment shown in FIG. 1, the end of portion 8 of connector 4 that is not connected to portion 6 has an opening 20 to which one end of a catheter is fitted. The other end of the catheter is connected to a patient. Thus, a fluid such as medication may be conveyed from connector 4 to a patient. Portions 6 and 8 of connector 4 have respective complementary opposing surfaces so that only portions 6 and 8 may be coupled to each other. This is to avoid mistaken coupling of either one of those portions with a different half portion, so as to prevent the conveying of an incorrect medication to the patient via the catheter. Filter 14 is provided in the FIG. 1 embodiment for filtration purposes and is not necessary for the practice of the instant invention, as evidenced by the direct coupling of connector 4 to adapter 2 as shown in the FIG. 2 embodiment.

During transport and before use, to maintain sterility, a cap 22 may be used to cover connector end 10 of connector 4. Similarly, connector 18 of filter 14 may be covered by a cap 24. A plug 26 that has a connector end 28 that may have the same configuration as connector end 10 is used to cover the end opening of adapter 2, that, as shown in FIG. 1, faces connector 18 of filter 14. A more detailed discussion of the complementary opposing surfaces of portions 6 and 8 of connector 4 may be gleaned from the disclosure of the above-mentioned U.S. Pat. No. 6,612,624, the disclosure of which being incorporated by reference herein.

With reference to FIG. 2, adapter 2 is shown to include an outer housing sleeve or a housing shroud 30 that has the shape of a cylinder with two opposed open ends 32 and 34. Adapter 2 further has an insert or an inner shroud 36 that fits into housing shroud 30 by way of its opening 32. A third component of the adapter 2 of the instant invention comprises a core insert, or simply core 38 that fits into housing shroud 30 by way of the latter's opening 34.

FIG. 3 shows adapter 2 in its assembled form with inner shroud 36 and core 38 respectively fittingly mated to housing shroud 30.

A perspective view of housing shroud 30 is shown in FIG. 4A. Together with the sectional views of FIGS. 4B and 4C and the end view of FIG. 4D, housing shroud 30 is shown to have a first or distal opening 32 and a second or proximal opening 34. As best shown in the sectional views of FIGS. 4B and 4C, a hub catch 40 made up of extending fingers 42 is provided at the proximal portion of housing shroud 30. Each of fingers 42 has a finger tip or catch surface 44 that extends toward the longitudinal axis 46 of cylindrical housing shroud 30 to form an opening 48 that has a smaller diameter than proximal opening 34. Finger tips 44 of the fingers 42 that make up hub catch 40 are chamfered in the direction of opening 34 and yet are flat when viewed from the direction of opening 32. Thus, the respective catch surfaces of fingers 42 face the inner shroud 36. At distal opening 32 of housing shroud 30 there is a lip 50. Opening 32 is reduced in diameter at location 52. As can be seen from the end view of FIG. 4D, which is viewed from opening 32, each of fingers 42, best represented by fingertips 44, is separated from its adjacent fingers by a notch 55 that provides additional flexibility to the fingers when core 38 is inserted to housing shroud 30 via opening 34. Also shown in FIG. 4D, as well as the cross-sectional views of FIGS. 4B and 4C, are a plurality of bumps 56 that extend inwardly toward longitudinal axis 46.

FIGS. 5A-5D show inner shroud 36 of the instant invention adapter. As shown, inner shroud 36 has a through bore 53 that extends from its distal end 54 to its proximal end 56. At its distal end there is a protrusion 58 formed circumferentially at its outer surface. Outer wall 60 extends from distal end 54 to proximal end 56, ending with a plurality of teeth 62 that extend longitudinally away from proximal end 56. Each of the teeth has an apex 62a, a ramp portion 62r and an upright portion 62u. Each of the teeth is separated from its adjacent teeth by a space 64. Inner shroud 36 is internally threaded from its proximal opening 53 through a major portion of the shroud, per indicated by designation 66.

Core 38 of the adapter of the instant invention is best shown in FIGS. 6A-6D. Core 38 comprises at its proximal portion a connector end, in the form of a luer fitting 68 that allows it to be coupled to a luer end of a medication providing device such as for example a syringe or medication pump. Extending from the proximal portion of core 38 is a circumferential flange 70 that has a diameter substantially the size of proximal opening 34 of housing shroud 30. A cylindrical central portion 72 extends from flange 70 to a shoulder flange 74 that has a flat rear surface 76 facing flange 70. Shoulder flange 74 is chamfered at an angle along its surface 78 so that the widest portion of shoulder flange 74 extends at an angle inwards towards longitudinal axis 46 until it joins the distal male portion 80. A bore 82 through core 38 extends from the tip of distal portion 80 to opening 84 at the proximal end of core 38.

In combination, the adapter of the instant invention has fitted into housing shroud 30 at its proximal opening 34 core 38 and at its distal opening 32 inner shroud 36. With reference to FIGS. 4A-4D, 5A-5D and 6A-6C, it can be seen that inner shroud 36 is mated to housing shroud 30. More particularly, the circumferential protuberance 58 of inner shroud 36 is press or snap fitted to space 51, i.e., a circumferential groove, formed at the distal end of housing shroud 30. Since the cross dimension of inner shroud 36 is configured to fit within space or circumferential groove 51 of housing shroud 30, once protuberance 58 is movably mated to space 51 and is retained by lip 50, inner shroud 26 is no longer removable from housing shroud 30. Protuberance 58 of inner shroud 36 is slidably movable within space 51 between reduced diameter location 52 and lip 50, per indicated by bi-directional arrow 57.

Inner shroud 36 may be biased relative to housing shroud 30 in the direction indicated by directional arrow 86 (FIG. 4B) when connector 4 is being coupled to adapter 2 via opening 53 of inner shroud 36. When connector 4 is being threadingly mated to inner shroud 36, a force is applied by the user, i.e., a torque in the direction to lock connector end 10 of connector 4 to the internal threaded portion 66 of inner shroud 36. The torque force, which is combined with a biasing forward force, causes inner shroud 36 to be pushed along the direction of directional arrow 86 so that teeth 62 of inner shroud 36 would come into contact with bumps 56 formed internally at housing shroud 30. Bumps 56 then act as a backstop to enable the user to threadingly mate connector 10 to inner shroud 36, and therefore adapter 2.

Once connector end 10 is fully mated to the threaded portion 66 of inner shroud 36, if connector 4 is rotated further in the direction of the locking torque movement, inner shroud 36 would pull away and rotate freely, as ramp portion 62r of teeth 62 would guide teeth 62 away from bumps 56. But if a counter torque were to be applied to connector 4 to rotate inner shroud 36 in a direction opposite to that of mating connector 4 to inner shroud 36, connector 4 is removable from inner shroud 36, as back portion 62b of each of teeth 62 acts against a side of a corresponding bump 56 to thereby prevent rotation of inner shroud 36 relative to housing shroud 30. As a result, connector 4 is removable from adapter 2 when it is rotated in a direction counter to the rotation needed to thread it into adapter 2.

Core 38 is fitted to housing shroud 30 via its proximal opening 34. As core 38 is pushed into housing shroud 30, the chamfered surface 78 of shoulder 74, since it is at a forward incline, is able to readily cause catch fingers 44 of housing shroud 30 to slightly flex, particularly since the adjacent fingers 44 are separated by slots or notches 55, so that shoulder 76 would pass opening 48 of hub catch 40. Once shoulder 74 fully passes the catches 44 of fingers 42, since its back surface is flat, core 38 is prevented by catch hub 48, more specifically by the plurality of fingers 42, from being removed or separated from housing shroud 30.

Distal opening 34, as best shown in the cross-sectional views of FIGS. 4B and 4C, has a cross section 35 that has the same diameter as flange 70. A ledge 37 at opening 34 prevents flange 70 from being pushed further into housing shroud 30, per directional arrow 88. Thus, once core 38 is fitted to housing shroud 30, it is non-removably fitted thereto. The cylindrical central portion 72, which is sandwiched by shoulder 76 and flange 70, is positioned within the proximal portion of housing shroud 30.

The nose portion 80 of core 38 is configured to have a length that allows it to be positioned within space 51 of housing shroud 30, as best shown in FIG. 3. Thus positioned, nose portion 80 is adaptable to mate with connector end 10 of connector 4, when connector 4 is mated to inner shroud 36. Once connector 4 is mated to inner shroud 36, a through path extending from opening 20 of connector 4 to opening 84 of core 38 is established to thereby enable fluid such as medication to pass from a medication providing device to the connector, and from there through the catheter connected thereto to the patient.

As core 38 is non-removably connected to housing shroud 30 by central portion 72 being rotatably mounted to catch hub 42, core 38 is rotatable freely either clockwise or counterclockwise relative to housing shroud 30. The respective dimensions of proximal opening 34 of housing shroud 30 and flange 70 may be manufactured to establish a predetermined friction between housing shroud 30 and core 38 to enable a user to readily connect a medication providing device, such as for example a conventional syringe or the connector of a medication pump, to luer connector 68 of core 38. But once the syringe is fully connected to core 38, due to the fact that core 38 is freely rotatable relative to housing shroud 30, the medication providing device could no longer be removed from adapter 2, as any rotational movement applied to the medication providing device would cause core 38 to rotate freely relative to housing shroud 30.

By thus preventing the detachment of the medication providing device from adapter 2 once it is connected to the luer connector end 68 of core 38, the adapter of the instant invention ensures that the medication in the medication providing device could only be conveyed to the connector that has a connector end that could mate correctly only with the connector end of the adapter, i.e., threaded connector portion 66 of inner shroud 36 for the embodiment being discussed. Of course, if connector 4 has a differently configured connector end 10, a corresponding connector end is needed at inner shroud 36 for properly mating therewith. Adapter 2 of the instant invention is therefore able to provide a bridge for connecting a medication providing device to the proper connector, to thereby ensure that a correct fluid pathway is established to convey the correct medication to the patient.

The invention claimed is:

1. A method of routing a medication from a medication providing device, comprising the steps of:
   a) providing a given medication conveying connector;
   b) providing an adapter having a shroud with one open end and an other open end;
   c) non-removably fitting an inner shroud to the one end of the shroud, the inner shroud having a connector end for enabling the inner shroud to be mated to the given medication conveying connector; and
   d) non-removably fitting a core to the other end of the shroud, the core having a through passage and a connector end for enabling the core to be mated to a connector of the medication providing device, the medication providing device once mated to the core is not removable from the core.

2. Method of claim 1, wherein the step c further comprises the step of:
   configuring the inner shroud to fit into the shroud such that the inner shroud rotates freely in one direction once the given medication conveying connector is mated thereto and the given connector is rotated in the one direction.

3. Method of claim 2, further comprising the step of:
   removing the given medication conveying connector from the inner shroud by rotating the medication providing device in a counter direction.

4. Method of claim 1, further comprising the step of:
configuring the core to be freely rotatable irrespective of whichever direction the medication providing device is turned once the medication providing device is mated to the core.

5. Method of claim 1, further comprising the steps of:
configuring a cylindrical central portion sandwiched by a circumferential shoulder and a circumferential flange for the core;
configuring an inner circumferential catch at the shroud; and
rotatably securing the central portion of the core to the shroud so that the shoulder and the flange would prevent the core from being removed from the shroud once the core is fitted to the shroud and the central portion is secured by the catch, and the core and the shroud being freely rotatable relative to each other.

6. Method of claim 5, wherein the circumferential catch comprises a hub catch, the method further comprising the steps of:
forming an aperture at the hub catch with a plurality of adjacent fingers, respective catch surfaces of the fingers facing the inner shroud;
configuring the fingers to allow the shoulder of the core to pass through the aperture when the core is fitted to the shroud and to prevent the shoulder from passing through the aperture in the reverse direction.

7. Method of claim 1, further comprising the steps of:
forming a protrusion circumferentially near the distal end the inner shroud;
mating the protrusion with a circumferential groove at the inner wall of the shroud to enable the inner shroud and the shroud to rotate relative to each other;
forming a plurality of extending teeth at a proximal end of the inner shroud; and
configuring the inner shroud to receive the given medication conveying connector.

8. Method of claim 7, further comprising the step of:
extending a plurality of bumps from the inner wall of the shroud toward a central longitudinal axis of the shroud, the bumps acting against the plurality of teeth of the inner shroud to prevent further rotational movement of the inner shroud relative to the shroud when the inner shroud is pressed with a forward biasing force along the longitudinal axis into the shroud after the given medication conveying connector has been rotated in a locking direction to mate to the inner shroud, wherein once the forward biasing force is removed from the inner shroud, the inner shroud is freely rotatable relative to the shroud when the given medication conveying connector is rotated in the locking direction.

9. A method of assembling an adapter for use with a medication providing device and a connector for providing medication to a patient, comprising the steps of:
a) providing a shroud;
b) fitting an inner shroud to the shroud, inner shroud having an opening for accepting a connecting end of the connector, the connector once mated to the inner shroud is freely rotatable in one direction and is removable from the inner shroud when rotated in a counter direction; and
c) fitting a core in the shroud to allow the medication to be routed from the medication providing device to the connector, the core having a proximal end to enable the medication providing device to directly connect thereto;
wherein the medication providing device is not removable from the core once it is connected to the proximal end.

10. Method of claim 9, wherein the step c comprises the step of:
configuring the core in the shroud to be freely rotatable relative to the shroud once the medication providing device is rotatably mated to the proximal end to prevent the medication providing device from being removed from the core once it is mated to the proximal end.

11. Method of claim 9, further comprising the steps of:
configuring the core to have a distal end, the proximal end and a cylindrical central portion connecting the proximal and distal ends, a shoulder circumferentially provided at where the distal end and the central portion are joined and a flange circumferentially provided at where the central portion and the proximal end are joined; and
configuring the shroud to have an inner circumferential catch whereat the central portion of the core is rotatably secured, the shoulder and the flange preventing the core from being removed from the shroud once the core is fitted to the shroud and the central portion is secured by the catch, the core and the shroud being freely rotatable relative to each other.

12. Method of claim 11, further comprising the steps of:
configuring the circumferential catch to have an aperture formed by a plurality of adjacent fingers with respective catch surfaces of the fingers facing the inner shroud; and
configuring the fingers to allow the shoulder of the core to pass through the aperture when the core is fitted to the shroud but prevents the shoulder from passing through the aperture in the reverse direction.

13. Method of claim 9, further comprising the steps of:
configuring the opening of the inner shroud at its distal end;
forming a protrusion circumferentially near the distal end; and
mating the protrusion with a circumferential groove at the inner wall of the shroud to enable the inner shroud and the shroud to rotate relative to each other.

14. Method of claim 9, wherein the step a comprises the step of:
forming a plurality of bumps at the shroud that extend from its inner wall toward a central longitudinal axis of the shroud, the bumps acting against a plurality of teeth at the inner shroud to prevent further rotational movement of the inner shroud relative to the shroud when the inner shroud is pressed with a forward biasing force along the longitudinal axis into the shroud after the connector has been rotated in a locking direction to connect to the inner shroud, wherein once the forward biasing force is removed from the connector, the connector is freely rotatable relative to the shroud when the connector is rotated in the locking direction.

15. Method of claim 14, further comprising the step of:
configuring each of the teeth of the inner shroud to have an upright edge that prevents the inner shroud from being rotated further in the locking direction when the inner shroud is pressed with the forward biasing force.

16. Method of claim 9, further comprising the step of:
configuring the connector to have two complementary opposing portions, a proximal one of the complementary portions having the connecting end for connection to the inner shroud.

* * * * *